United States Patent
De Man et al.

(10) Patent No.: US 7,372,934 B2
(45) Date of Patent: May 13, 2008

(54) METHOD FOR PERFORMING IMAGE RECONSTRUCTION USING HYBRID COMPUTED TOMOGRAPHY DETECTORS

(75) Inventors: Bruno Kristiaan Bernard De Man, Clifton Park, NY (US); Samit Kumar Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 4 days.

(21) Appl. No.: 11/317,841

(22) Filed: Dec. 22, 2005

(65) Prior Publication Data

US 2007/0147574 A1   Jun. 28, 2007

(51) Int. Cl.
*H05G 1/60* (2006.01)

(52) U.S. Cl. .................. 378/4; 378/98.12; 378/901; 250/370.09

(58) Field of Classification Search ............ 378/38–40, 378/98.12, 210, 901; 250/370.09, 370.11
See application file for complete search history.

(56) References Cited

U.S. PATENT DOCUMENTS

| | | | |
|---|---|---|---|
| 5,376,795 A * | 12/1994 | Hasegawa et al. ..... 250/363.04 |
| 5,742,660 A * | 4/1998 | Majewski et al. ......... 378/98.9 |
| 6,819,738 B2 | 11/2004 | Hoffman ..................... 378/19 |
| 6,904,118 B2 | 6/2005 | Wu et al. ....................... 378/5 |
| 7,272,429 B2* | 9/2007 | Walker et al. ............. 600/407 |
| 2004/0101104 A1* | 5/2004 | Avinash et al. ......... 378/98.12 |
| 2005/0061985 A1* | 3/2005 | Hoffman ................ 250/370.01 |
| 2005/0173641 A1* | 8/2005 | Unger et al. .......... 250/370.09 |
| 2006/0049357 A1* | 3/2006 | Tumer .................. 250/363.03 |
| 2007/0019782 A1* | 1/2007 | Van Stevendaal et al. ...... 378/6 |

* cited by examiner

*Primary Examiner*—Courtney Thomas
*Assistant Examiner*—Alexander H Taningco
(74) *Attorney, Agent, or Firm*—Jason K. Klindtworth; Curtis B. Brueske

(57) ABSTRACT

A method for acquiring an image data set comprising energy integrating (EI) and energy discriminating (ED) data measurements is provided. The method comprises obtaining EI measurement data and ED measurement data during an acquisition cycle. The method then comprises combining the EI measurement data and the ED measurement data before, during or after reconstruction. Finally the method comprises performing reconstruction on the original or combined datasets to obtain one or more of an EI image and one or more ED component images.

18 Claims, 5 Drawing Sheets

METHOD FOR PERFORMING IMAGE RECONSTRUCTION USING HYBRID COMPUTED TOMOGRAPHY DETECTORS

BACKGROUND

The invention relates generally to the field of image reconstruction. In particular, the invention relates to techniques for performing image reconstruction using hybrid computed tomography (CT) detectors.

CT imaging systems measure the intensity of X-ray beams passed through a patient from numerous angles. With sufficient angular coverage around the patient, cross-sectional images can be formed revealing the inner structure of the scanned object. The images are typically displayed on a cathode ray tube or a computer screen, and may be printed or reproduced on film. A virtual 3-D image may also be produced by a CT examination.

CT scanners operate by projecting X-ray beams from an X-ray source through an attenuating object, such as a patient. The X-ray beams may be collimated between the source and the object into a fan or cone shape, depending on the configuration of the detector optimal patient exposure, or other factors. The attenuated beams are then detected by a set of detector elements. The detector element produces a signal based on the intensity of the X-ray beams. The measured data are then processed to represent the line integrals of the attenuation coefficients of the object along the ray paths. The processed data are typically called projections. By using reconstruction techniques, such as filtered backprojection, cross-sectional images are formulated from the projections. Adjacent cross-sectional images may be displayed together to render a volume representing the imaged region of the object or patient.

As will be appreciated by those skilled in the art, the attenuation coefficient of a material is a function of two separate events that may occur when an X-ray beam passes through a given length of the material. The first event is known as Compton scatter and denotes the tendency of an X-ray photon passing through the length of the material to be scattered or diverted from the original beam path, with a resultant change in energy. The second event is known as photoelectric absorption and denotes the tendency of an X-ray photon passing through the length of the material to be absorbed by the material.

As one might expect, different materials differ in their scatter and absorption properties, resulting in different attenuation coefficients for different materials. In particular, the probability of Compton scattering depends in part on the electron density of the imaged material and the probability of photoelectric absorption depends in part on the atomic number of the imaged material, i.e., the greater the atomic number, the greater the likelihood of absorption. Furthermore, both the Compton scattering effect and photoelectric absorption depend in part on the energy of the X-ray beam. As a result, materials can be distinguished from one another based upon the relative importance of the photoelectric absorption and Compton scattering effects in X-ray attenuation by the material. In particular, measurement of the attenuation produced by a material at two or more X-ray energy levels or spectra, i.e., multi-energy or multi-spectral CT, may allow for respective Compton scattering and photoelectric absorption contributions to be quantified for a material at the X-ray energy levels employed.

Multi-energy CT scanning refers to the process of acquiring X-ray transmission measurements with two different effective X-ray energies. Often this is achieved by combining measurements at two or more tube voltages (dual kVp). Using two measurements of two different known effective energies it is possible to extract information on tissue and/or material composition. A common strategy is to separate the object into bone equivalent and soft tissue equivalent absorbers. Multi-energy scanning is based upon the principle that in the diagnostic X-ray energy range, essentially all X-ray interactions are either through photoelectric absorption or Compton scattering, which have different energy dependence. These in turn have different dependence on atomic number and electron density. As mentioned above, the probability of Compton scattering is dependent on the X-ray energy and the electron density, while the probability of photoelectric absorption increases rapidly with atomic number and decreases rapidly with increasing photon energy.

Energy discriminating (ED) detectors are generally used in multi-energy CT scanning systems to provide information regarding the energy-distribution of the detected photons, by producing two or more signals corresponding to two or more energy intervals, such as, for example a high energy signal and a low energy signal. As will be appreciated by those skilled in the art, ED detectors provide spatial information in conjunction with information regarding the physical density and/or effective atomic number of the material or materials within the imaging volume. Using the spatial and density and/or atomic number information, an operator may reconstruct images that predominantly display selected materials, such as bone, soft tissue, or contrast agent, which differ in their atomic number or density. In this manner, a bone image, a soft tissue image, a contrast agent image, and so forth may be reconstructed which predominantly displays the material of interest. These images may in turn be associated to form a volume rendering of the material of interest which may be useful in determining bone density or deterioration, soft tissue damage, contrast agent perfusion, and so forth. ED detectors may be used with a single source energy or with multiple source energies similar to a dual kVp CT system.

On the other hand, conventional CT detectors are referred to as Energy Integrating (EI) detectors. EI detectors produce an electronic signal that is proportional to the total amount of absorbed X-ray energy in each view. Consequently, the detector signal does not contain any information regarding the energy distribution of the individual photons.

A number of reconstruction techniques have been proposed that either use energy integrating (EI) detectors or energy discriminating (ED) detectors to reconstruct image data. Reconstruction using ED detectors comprises performing material decomposition on the projection measurements, during image reconstruction, or after image reconstruction. With the pre-reconstruction decomposition, material specific (e.g. bone and soft tissue, water and bone, water and barium or Compton scatter and Photo electric) projections are computed at each view angle and from each set, material specific images are reconstructed. An advantage of this approach is that beam hardening artifacts are prevented. With post-reconstruction multi-energy processing, each image may have beam hardening artifacts that are not removed in the material decomposition.

It would be desirable to develop a technique that combines the energy information provided by ED detector cells with the high flux capability and high signal to noise (SNR) ratio provided by EI detector cells for reconstructing image data in a CT system. In addition, it would be desirable to develop techniques for reconstructing image data comprising EI measurement data and ED measurement data using a CT detector comprising a combination of EI detector cells and ED detector cells.

BRIEF DESCRIPTION

Embodiments of the present invention address this and other needs. In one embodiment, a method for acquiring an image data set comprising energy integrating (EI) and energy discriminating (ED) data measurements is provided. The method comprises obtaining EI measurement data and ED measurement data during an acquisition cycle and combining and reconstructing the EI measurement data and the ED measurement data in a selected manner to generate at least one ED component image.

In a second embodiment, a method for acquiring an image data set comprising energy integrating (EI) and energy discriminating (ED) data measurements is provided. The method comprises obtaining EI measurement data and ED measurement data during an acquisition cycle. The method then comprises performing a first reconstruction on the EI measurement data to obtain an EI image and performing a second reconstruction on the ED measurement data to obtain at least one ED component image. Then, the method comprises combining the EI image and the at least one ED component image to obtain at least one of an updated ED component image or a combined ED and EI image.

In a third embodiment, a method for acquiring an image dataset comprising energy integrating (EI) and energy discriminating (ED) data measurements is provided. The method comprises obtaining EI measurement data and ED measurement data during an acquisition cycle. Then, the method comprises selectively combining the EI measurement data and the ED measurement data and generating at least one of an EI dataset and one or more ED component datasets based on the combined EI measurement data and the ED measurement data. The method then comprises performing a reconstruction based on the EI dataset and/or the one or more ED component datasets to generate at least one of an EI reconstructed image and one or more ED component images.

In a fourth embodiment, a method for acquiring an image dataset comprising energy integrating (EI) and energy discriminating (ED) data measurements is provided. The method comprises obtaining EI measurement data and ED measurement data during an acquisition cycle. The method then comprises performing a first reconstruction based on the EI measurement data to generate an EI image and performing a second reconstruction based on the ED measurement data and the EI image to generate one or more ED component images.

In a fifth embodiment, a method for acquiring an image dataset comprising energy integrating (EI) and energy discriminating (ED) data measurements is provided. The method comprises obtaining EI measurement data and ED measurement data during an acquisition cycle. Then, the method comprises performing a first reconstruction based on the EI measurement data to generate an EI image and applying a partitioning algorithm on the EI image to generate a partitioned image. The method then comprises performing a second reconstruction based on the ED measurement data and the partitioned image to generate one or more ED component images.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
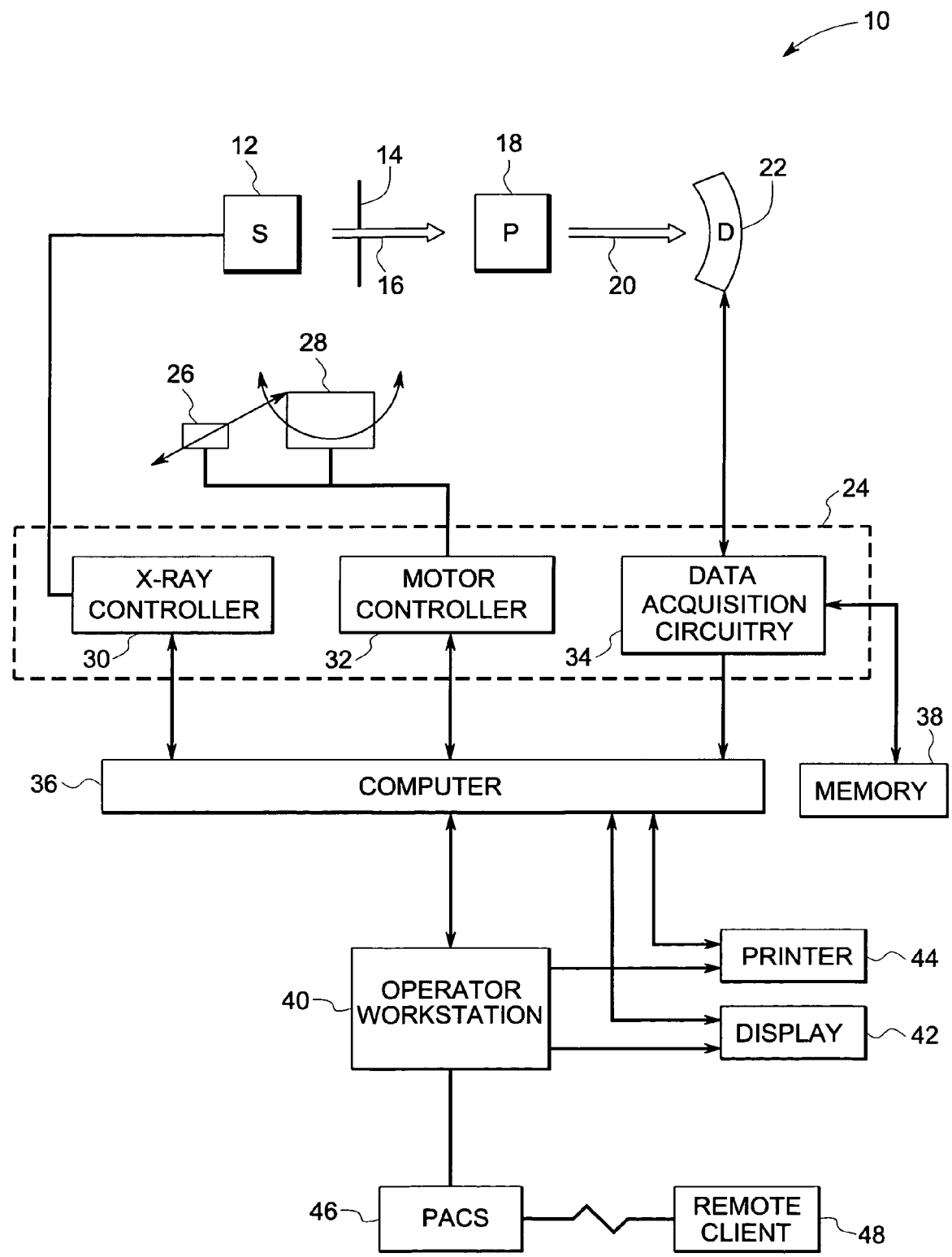
FIG. 1 illustrates diagrammatically an imaging system for acquiring and processing image data in accordance with aspects of the present technique.

FIG. 1 illustrates diagrammatically an imaging system 10 for acquiring and processing image data in accordance with aspects of the present technique. In the, illustrated embodiment, system 10 is a multi-energy computed tomography (ME-CT) system designed to acquire image data at two or more X-ray energy levels or spectra and to process the image data for display and analysis in accordance with the present technique. The imaging system 10 may be designed to acquire image data at a single X-ray source spectrum using a detector with energy resolution for the energy discriminating (ED) portion, which allows the energy level of each detected photon to be assessed. In the embodiment illustrated in FIG. 1, imaging system 10 includes a source of X-ray radiation 12 positioned adjacent to a collimator 14. In this exemplary embodiment, the source 12 of X-ray radiation is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject.

Figure 2:
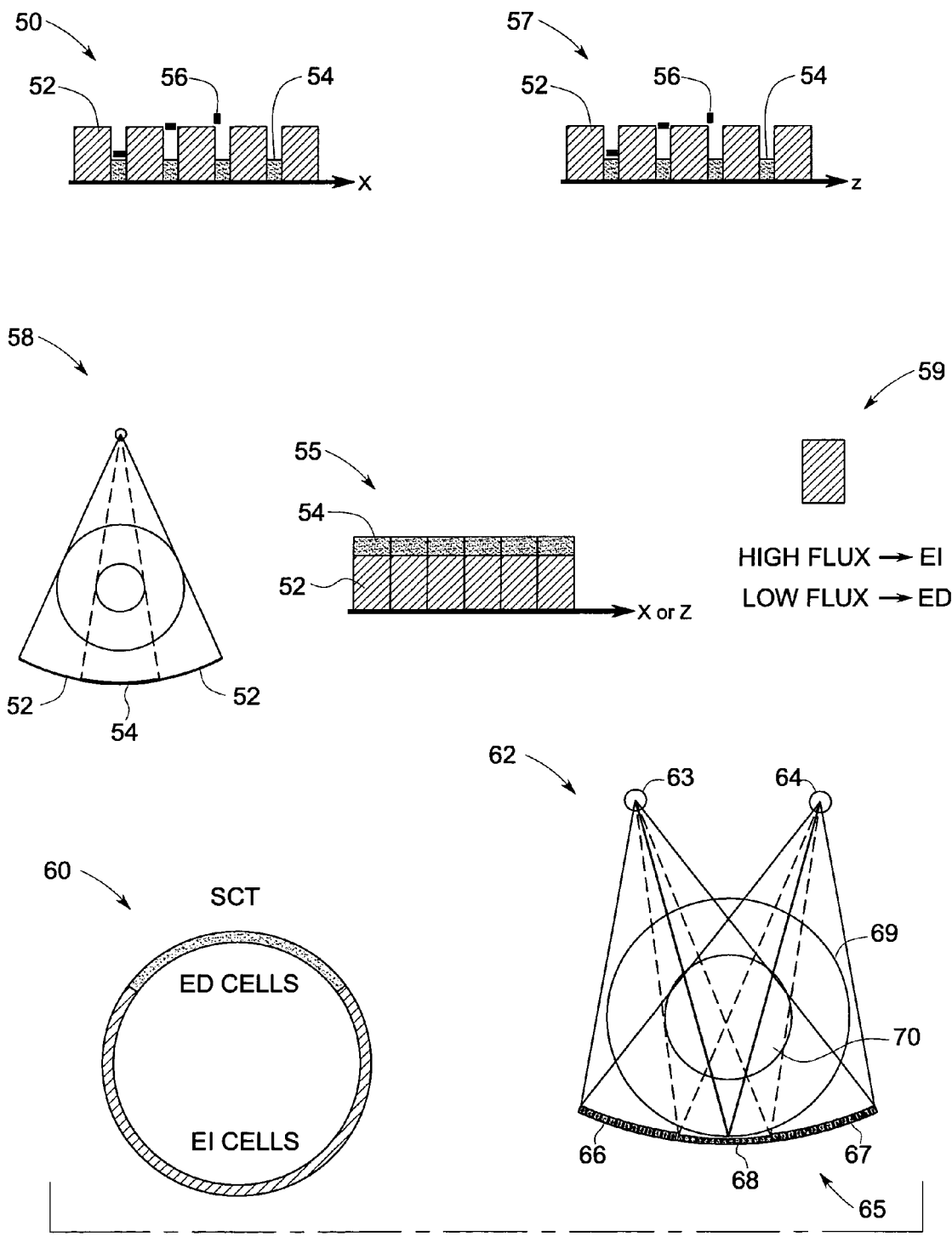
FIG. 2 illustrates exemplary hybrid detector cell configurations for reconstructing image data comprising energy integrating (EI) measurements and energy discriminating (ED) measurements acquired by the imaging system of FIG. 1.

In a particular embodiment, the detector 22 is a hybrid detector. As used herein, a "hybrid detector" refers to a detector that includes a combination of one or more energy integrating (EI) detector cells and one or more energy discriminating (ED) detector cells arranged in a number of configurations. FIG. 2 illustrates some exemplary hybrid detector configurations employed by embodiments of the present technique for reconstructing image data. As is known to those skilled in the art, energy integrating (EI) detectors produce an electronic signal that is proportional to the total amount of absorbed X-ray energy in each view. Consequently, the detector signal does not contain any information regarding the energy distribution of the individual photons. Energy discriminating (ED) detectors provide information regarding the energy distribution of the detected photons, by producing two or more signals corresponding to two or more energy intervals, such as, for example a high energy signal and a low energy signal.

A system controller 24 may control the source 12. The system controller 24 typically furnishes both power, and control signals for CT examination sequences. Moreover, the detector 22 is coupled to the system controller 24, which controls the acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12 and may determine what X-ray energy level or spectrum the source 12 emits. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

An operator may control the system 10 via the input devices. Thus, the operator may observe the reconstructed image and other data relevant to the system from computer 36, initiate imaging, and so forth. Similarly, a display 42 coupled to the operator workstation 40 may allow an operator to observe the reconstructed image and to control imaging. Additionally, a reconstructed image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote client 48, radiology department information system (RIS), hospital information system (HIS) or to an internal or external network, so that others at different locations may gain access to the image and to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

FIG. 2 illustrates exemplary hybrid detector cell configurations for reconstructing image data comprising energy integrating (EI) measurements and energy discriminating (ED) measurements acquired by the imaging system of FIG. 1. Reference numeral 50 illustrates a hybrid detector cell configuration including one or more Energy Integrating (EI) detector cells 52 and one or more Energy Discriminating (ED) detector cells 54, arranged in an interleaved fashion along the X-axis. In a particular embodiment, the interleaved arrangement of detector cells includes an arrangement of EI cells 52 and ED cells 54 in alternating rows, alternating columns or in a checkerboard fashion. An attenuator or a movable collimator blade or filter 56 is configured to block one or more of the ED detector cells 54. Reference numeral 57 illustrates another hybrid detector cell configuration including one or more EI detector cells 52 and one or more ED detector cells 54, arranged in an interleaved fashion along the Z-axis. Reference numeral 58 illustrates a hybrid detector cell configuration including a central portion of ED detector cells 54 surrounded by EI detector cells 52. Reference numeral 55 illustrates a multi-layer hybrid detector cell configuration comprising a top layer of ED detector cells 54 and a bottom layer of EI detector cells 52. In this configuration, the ED layer may be made substantially thin to avoid saturation so that the photons that penetrate the ED layer get detected by the EI layer. Reference numeral 59 illustrates a hybrid detector cell configuration wherein the detector cells are configured to operate in both ED and EI mode. In an exemplary operation, the cells comprising the hybrid detector cell configuration 59 are configured to function as ED cells 54 when the flux is low, and function as EI cells 52 when the flux is high. In another exemplary operation, the detector cells may switch from ED mode to EI mode in a deterministic fashion, such as, for example, a low mA view resulting in ED measurements followed by a high mA view resulting in EI measurements. The resulting dataset is a hybrid dataset comprising ED views and EI views. Reference numeral 60 illustrates yet another hybrid detector cell configuration, in which the EI cells 52 and the ED cells 54 are arranged in a stationary CT configuration. A plurality of EI detector cells 52 may be arranged along the detector array 22. Furthermore, a plurality of ED detector cells 54 may be arranged adjacent to the plurality of EI detector cells 52 and along the detector array 22. As will be appreciated, a stationary CT system includes one or more stationary sources of radiation (not shown). Generally, in many embodiments, the EI detector portions and the ED detector portions can also be spatially separated from each other (possibly even with separate sources), resulting in a hybrid system as compared to a hybrid detector.

Reference numeral 62 illustrates another exemplary hybrid detector cell configuration of a combined detector arc 65. In this embodiment, a first source of radiation 63 and a second source of radiation 64 may be employed. It may be noted that the first source of radiation 63 and the second source of radiation 64 may be illuminated sequentially, in one embodiment. Furthermore, in accordance with aspects of the present technique, more than two sources of radiation may also be employed. The detector arc 65 may include a first side wing 66, a second side wing 67 and a center portion 68 disposed between the first and second side wings 66, 67. In a presently contemplated configuration, the first side wing 66 may include a first set of a plurality of energy integrating detector elements. In a similar fashion, the second wing 67 may include a second set of a plurality of energy integrating detector elements. Furthermore, the center portion 68 may include a plurality of energy discriminating detector elements. Reference numeral 69 is representative of a relatively large region of interest, while reference numeral 70 is representative of a relatively small region of interest. In accordance with exemplary aspects of the present technique, a portion of the X-ray beam having a relatively large field of view may be measured by the plurality of energy integrating detector elements, while a portion of the X-ray beam having a relatively small field of view may be measured by the plurality of energy discriminating detector elements.

The following flowcharts illustrate various embodiments for combining EI measurement data and ED measurement data in a selected manner to generate an EI image and one or more ED component images, using one or more of the hybrid detector configurations illustrated and described in FIG. 2. As is known to those skilled in the art, each voxel comprising the ED component images may be characterized by a photo-electric absorption density/weight and a Compton scatter density/weight. Realizing that X-ray attenuation is mainly due to photo-electric absorption and Compton scatter, the linear attenuation in a voxel may be characterized by two parameters $\phi$ and $\theta$, wherein $\phi$ represents the amount of photo-electric absorption in a given tissue or voxel and $\theta$ represents the Compton scatter in a given tissue or voxel. Given that the energy dependences of the effects due to photo-electric absorption ($\Phi(E)$) and Compton scatter ($\Theta(E)$) are known and independent of material, the linear attenuation of a voxel may be represented as shown in equation (1) below.

$$\mu(E) = \phi \cdot \Phi(E) + \theta \cdot \Theta(E) \tag{1}$$

Since the attenuation of every material may be represented as a linear combination of the two basis functions, $\Phi(E)$ and $\Theta(E)$, any two materials whose $\phi$ and $\theta$ are linearly independent may be chosen to define a new set of basis functions. Typical examples of such materials include, but are not limited to, water and bone, or bone and iodine. For example, a decompostion of water and bone may be represented by equation (2), as shown below.

$$\mu(E) = w \cdot W(E) + b \cdot B(E) \tag{2}$$

where w represents water and b represents bone. Equation (2) may be transformed into equation (1) (or vice versa) by substituting:

$$W(E) = c1 \cdot \Phi(E) + c2 \cdot \Theta(E) \tag{3}$$

$$B(E) = c3 \cdot \Phi(E) + c4 \cdot \Theta(E) \tag{4}$$

where $c1$, $c2$, $c3$, and $c4$ are empirically defined coefficients. Alternately, ideal materials may be used: e.g., one theoretical material that has no photoelectric absorption and only Compton interactions, and a second theoretical material that has no Compton interactions and only photoelectric absorption. Any physical material can then be represented as a linear combination of these two ideal materials.

Therefore, in accordance with aspects of the present technique, generating one or more ED component images includes determining one or more of a photo-electric absorption portion and a Compton scatter portion for each voxel comprising the ED component images, based on the ED measurements. As used herein, an ED component image may include, but is not limited to, a Compton scatter component image, a photo-electric component image, a water component image, or a bone component image. For other applications, it may be necessary to model additional physical processes, such as the presence of K-edges in the absorption spectra.

Figure 3:
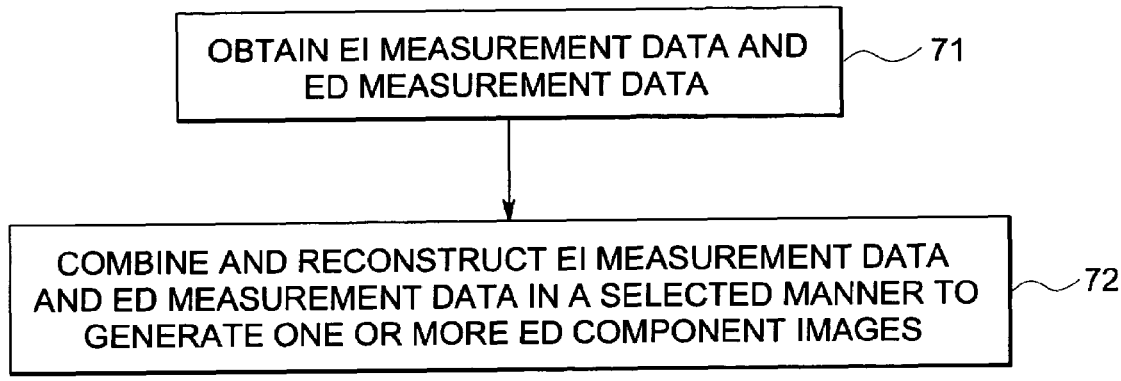
FIG. 3 is a flowchart of exemplary steps including exemplary logic for reconstructing image data using a hybrid CT detector, in accordance with one embodiment of the present invention.

FIG. 3 is a flowchart of exemplary steps including exemplary logic for reconstructing image data using a hybrid CT detector, in accordance with one embodiment of the present invention. In step 71, EI measurement data and ED measurement data are obtained during an acquisition cycle. In step 72, the EI measurement data and the ED measurement data are combined and reconstructed in a selected manner to generate one or more ED component images. In one embodiment, combining the EI measurement data and the ED measurement data comprises performing an iterative reconstruction on the ED measurement data and the EI measurement data to generate one or more ED component images. Examples of iterative reconstruction techniques include, but are not limited to maximum likelihood (ML) techniques, maximum a posteriori (MAP) techniques, weighted least squares (WLS) techniques and penalized weighted lease squares (PWLS) techniques. The ED component images may be further processed to generate at least one of a linear attenuation coefficient image, a CT number image or a single material image. In one embodiment, the ED component image is representative of at least one of attenuation due to Compton Scatter or attenuation due to a photo-electric effect.

Figure 4:
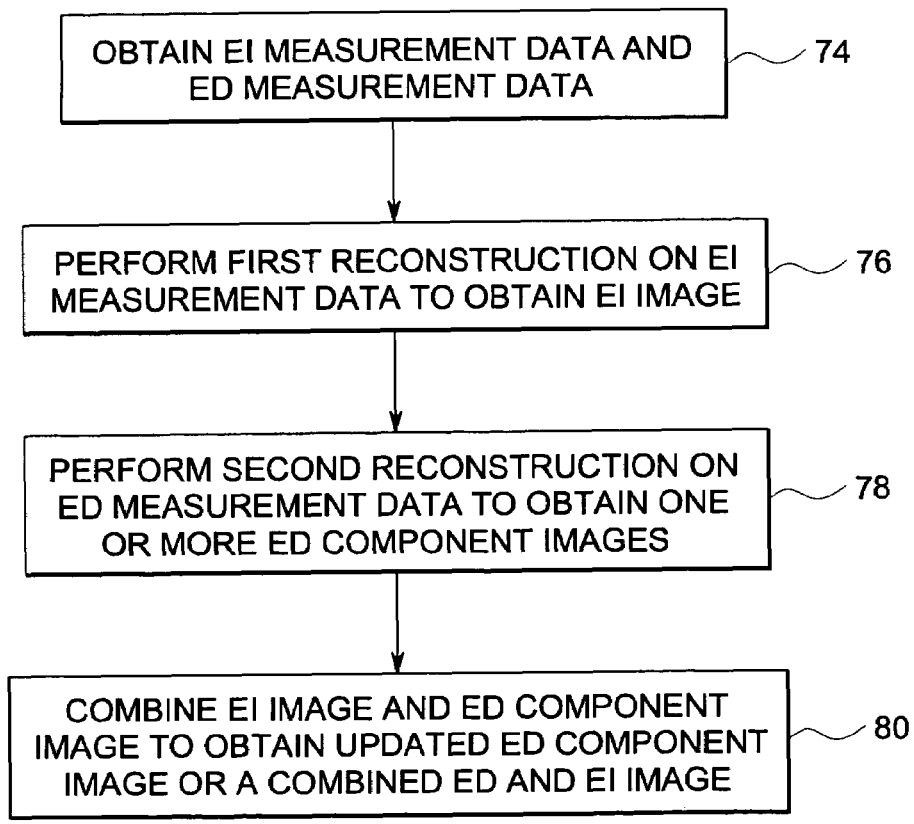
FIG. 4 is a flowchart of exemplary steps including exemplary logic for reconstructing image data using a hybrid CT detector, in accordance with an alternate embodiment of the present invention.

FIG. 4 is a flowchart of exemplary steps including exemplary logic for reconstructing image data using a hybrid CT detector, in accordance with an alternate embodiment of the present invention. In step 74, EI measurement data and ED measurement data are obtained during an acquisition cycle. In step 76, a first reconstruction is performed on the EI measurement data to obtain an EI image. In step 78, a second reconstruction is performed on the ED measurement data to obtain one or more ED component images. In step 80, the EI image and the ED component images are combined to obtain an updated ED component image or a combined ED and EI image. As will be appreciated by those skilled in the art, the use of a hybrid detector, in accordance with embodiments of the present invention, results in the generation of an ED image that may have artifacts or missing frequencies, due to the unavailability of complete ED data. In accordance with one embodiment, the EI images and the ED images are combined to compensate for the missing information or the artifacts in either of the two. In one embodiment, the combining comprises patching the missing ED portions (for example, in the case where the ED data results in truncation of the field of view) with scaled versions of the EI image. In another embodiment, the combining comprises using the EI image for high frequencies to patch the missing high frequencies in the ED image. In yet another embodiment, the ED image and the EI image may be combined by overlaying different color maps. Further, in a particular embodiment, the first reconstruction may be performed using a filtered backprojection reconstruction technique to obtain the EI image. The second reconstruction may be performed using an iterative reconstruction technique to generate the one or more ED component images.

Figure 5:
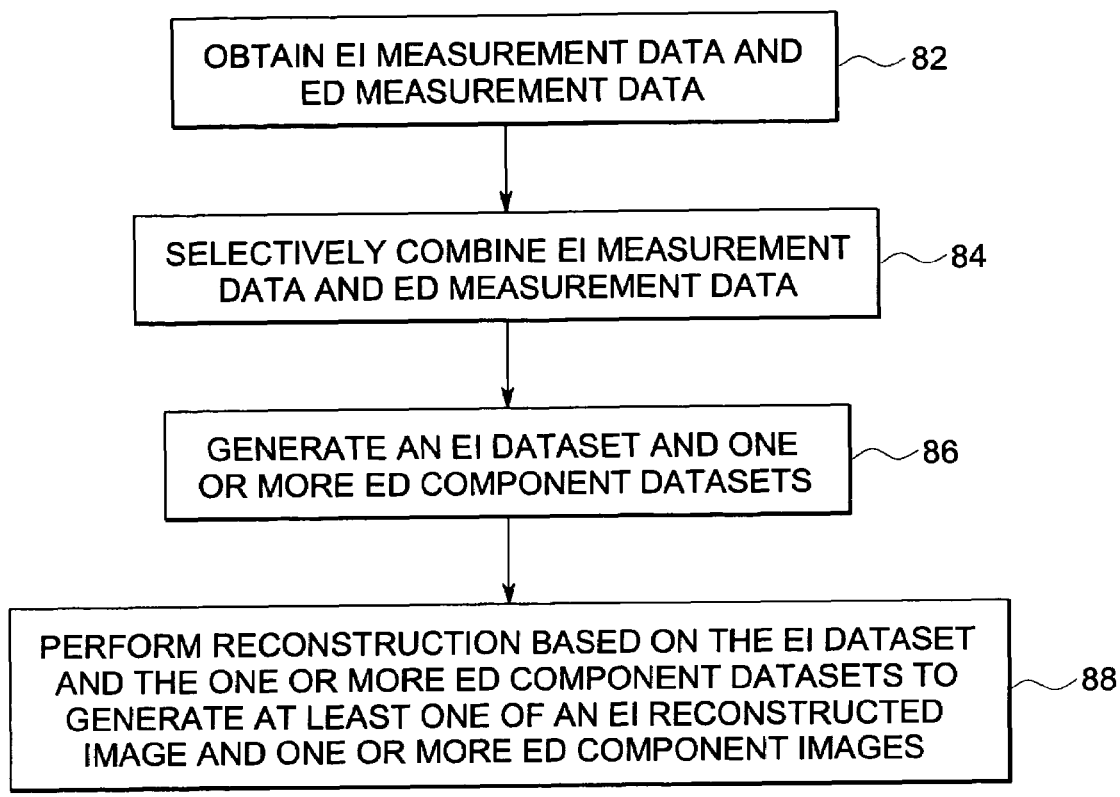
FIG. 5 is a flowchart of exemplary steps including exemplary logic for reconstructing image data using a hybrid CT detector, in accordance with another embodiment of the present invention.

FIG. 5 is a flowchart of exemplary steps including exemplary logic for reconstructing image data using a hybrid CT detector, in accordance with another embodiment of the present invention. In step 82, EI measurement data and ED measurement data are obtained during an acquisition cycle. In step 84, the EI measurement data and the ED measurement data are selectively combined. In one embodiment, selectively combining the EI measurement data and the ED measurement data comprises patching the missing ED portions (for example, in the case where the ED data results in truncation of the field of view) with scaled versions of the EI data. In another embodiment, the combining comprises using the EI data for high frequencies to patch the missing high frequencies in the ED data. In step 86, an EI dataset and/or one or more ED component datasets are generated based on the combined EI measurement data and the ED measurement data. In step 88, a reconstruction is performed based on the EI dataset and the one or more ED component datasets to generate at least one of an EI reconstructed image and one or more ED component images. Further, in one embodiment, a filtered backprojection reconstruction is performed on the EI dataset to generate the EI reconstructed image and an iterative reconstruction is performed on the ED component datasets to generate one or more ED component images.

Figure 6:
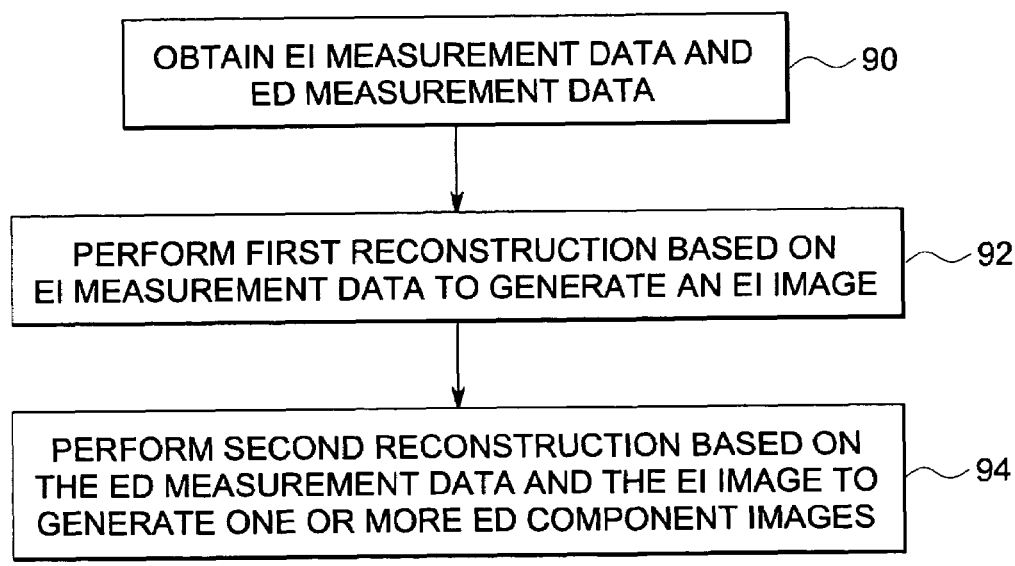
FIG. 6 is a flowchart of exemplary steps including exemplary logic for reconstructing image data using a hybrid CT detector, in accordance with yet another embodiment of the present invention.

FIG. 6 is a flowchart of exemplary steps including exemplary logic for reconstructing image data using a hybrid CT detector, in accordance with yet another embodiment of the present invention. In step 90, EI measurement data and ED measurement data are obtained during an acquisition cycle. In step 92, a first reconstruction is performed based on the EI measurement data to generate an EI image. In step 94, a second reconstruction is performed based on the ED measurement data and the EI image to generate one or more ED component images. In a particular embodiment, the EI image is used as a starting point or as prior information for reconstructing the ED image. The prior information compensates for sparse or missing data in the ED image. Further, the EI image may be transformed using a transformation function to result in an initial estimate for the iterative reconstruction of the one or more ED component images. The transformed EI image may be used during the iterative reconstruction process either as a constraint on the ED image or as an absolute intensity prior to the iterative reconstruction of the ED image. Further, in a particular embodiment, the first reconstruction may be performed using a filtered backprojection reconstruction to obtain the EI image. The second reconstruction may be performed using an iterative reconstruction to generate one or more ED component images. In one embodiment, the second reconstruction includes scaling the EI image, using the EI image as an initial estimate in the iterative reconstruction of the ED component images, or using the EI image as prior information in the iterative reconstruction of the ED component images. In another embodiment, the second reconstruction reconstructs a second component that is perpendicular to the first in the two-material space, while keeping the first component fixed. For example, if the first component represents density of water, then the second component has a zero water density.

Figure 7:
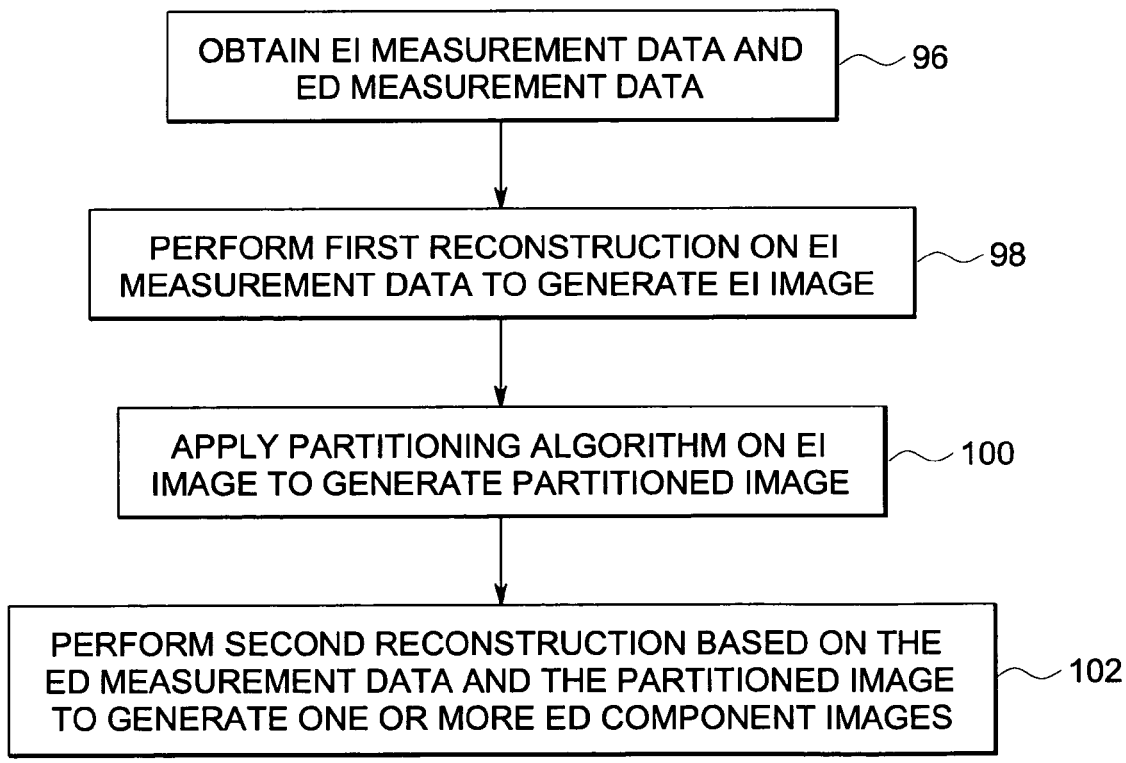
FIG. 7 is a flowchart of exemplary steps including exemplary logic for reconstructing image data using a hybrid CT detector, in accordance with yet another embodiment of the present invention.

FIG. 7 is a flowchart of exemplary steps including exemplary logic for reconstructing image data using a hybrid CT detector, in accordance with yet another embodiment of the present invention. In step 96, EI measurement data and ED measurement data are obtained during an acquisition cycle. In step 98, a first reconstruction is performed on the EI measurement data to generate an EI image. In step 100, a partitioning algorithm is applied on the EI image to generate a partitioned image. In one embodiment, the partitioning algorithm includes segmenting the EI image into at least one of bone regions, soft tissue regions or iodine regions. As will be appreciated by those skilled in the art, partitioning algorithms (or segmentation algorithms) are based on simple thresholding or techniques such as the zero crossing of the second-derivative. Partitioning algorithms may also use anatomical information in the form of, for example, atlases to assist in the partitioning step. In step 102, a second reconstruction is performed based on the ED measurement data and the partitioned image to generate one or more ED component images. In one embodiment, the second reconstruction includes scaling the EI image, using the EI image as an initial estimate in the iterative reconstruction of the ED component images, or using the EI image as prior information in the iterative reconstruction of the ED component images. In another embodiment, the second reconstruction may reconstruct each region with specific tissue classes (for example, iodine and bone) as identified by the partitioning algorithm.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for acquiring an image data set comprising energy integrating (EI) and energy discriminating (ED) data measurements, the method comprising:
   obtaining EI measurement data and ED measurement data during an acquisition cycle;
   combining the EI measurement data and the ED measurement data in a selected manner, wherein the combining comprises:
      performing a first reconstruction based on the EI measurement data to generate an EI image;
      performing a second reconstruction based on the ED measurement data to generate at least one ED component image; and
      combining the EI image and the at least one ED component image to generate at least one of an updated ED component image or a combined ED and EI image.

2. The method of claim 1, further comprising processing the ED component images to generate at least one of a linear attenuation coefficient image, a CT number image or a single material image.

3. The method of claim 1, wherein the combining comprises performing an iterative reconstruction on the ED measurement data and the EI measurement data to generate the at least one ED component image.

4. The method of claim 3, wherein the ED component image is representative of at least one of attenuation due to Compton Scatter or attenuation due to a photo-electric effect.

5. The method of claim 3, wherein the iterative reconstruction comprises at least one of a maximum likelihood (ML) technique, a maximum a posteriori (MAP) technique, a weighted least squares (WLS) technique, or a penalized weighted least squares (PWLS) technique.

6. The method of claim 1, wherein the combining further comprises:
   performing a first reconstruction based on the EI measurement data to generate an EI image; and
   performing a second reconstruction based on the ED measurement data and the EI image to generate one or more ED component images.

7. The method of claim 1, wherein the combining further comprises:
   performing a first reconstruction based on the EI measurement data to generate an EI image;
   applying a partitioning algorithm on the EI image to generate a partitioned image; and
   performing a second reconstruction based on the ED measurement data and the partitioned image to generate one or more ED component images.

8. A method for acquiring an image dataset comprising energy integrating (EI) and energy discriminating (ED) data measurements, the method comprising:
   obtaining EI measurement data and ED measurement data during an acquisition cycle;
   selectively combining the EI measurement data and the ED measurement data;
   generating at least one of an EI dataset and one or more ED component datasets based on the combined EI measurement data and the ED measurement data; and
   performing a reconstruction based on the EI dataset and the one or more ED component datasets to generate at least one of an EI reconstructed image and one or more ED component images.

9. The method of claim 8, wherein the ED component image is representative of at least one of attenuation due to Compton Scatter or attenuation due to a photo-electric effect.

10. A method for acquiring an image dataset comprising energy integrating (EI) and energy discriminating (ED) data measurements, the method comprising:
    obtaining EI measurement data and ED measurement data during an acquisition cycle;
    performing a first reconstruction based on the EI measurement data to generate an EI image; and
    performing a second reconstruction based on the ED measurement data and the EI image to generate one or more ED component images.

11. The method of claim 10, wherein the second reconstruction comprises performing an iterative reconstruction to generate one or more ED component images.

12. The method of claim 11, wherein the second reconstruction comprises at least one of scaling the EI image, using the EI image as an initial estimate in the iterative reconstruction of the ED component images, or using the EI image as prior information in the iterative reconstruction of the ED component images.

13. The method of claim 10, wherein the ED component image is representative of at least one of attenuation due to Compton Scatter or attenuation due to a photo-electric effect.

14. A method for acquiring an image dataset comprising energy integrating (EI) and energy discriminating (ED) data measurements, the method comprising:
    obtaining EI measurement data and ED measurement data during an acquisition cycle;
    performing a first reconstruction based on the EI measurement data to generate an EI image;
    applying a partitioning algorithm on the EI image to generate a partitioned image; and
    performing a second reconstruction based on the ED measurement data and the partitioned image to generate one or more ED component images.

15. The method of claim 14, wherein the partitioning algorithm includes segmenting the EI image into at least one of bone regions, soft tissue regions or iodine regions.

16. The method of claim 14, wherein the second reconstruction comprises performing an iterative reconstruction on the ED measurement data to generate the ED reconstructed image.

17. The method of claim 16, wherein the second reconstruction comprises at least one of scaling the EI image, using the EI image as an initial estimate in the iterative reconstruction of the ED component images, or using the EI image as prior information in the iterative reconstruction of the ED component images.

18. The method of claim 14, wherein the ED component image is representative of at least one of attenuation due to Compton Scatter or attenuation due to a photo-electric effect.

* * * * *